United States Patent [19]

Rizk

[11] 4,112,934
[45] Sep. 12, 1978

[54] COMBINATION ALVEOLAR RIDGE PROTECTOR AND ANESTHETIC ADMINISTRATION AID

[76] Inventor: Samy F. Rizk, 1601-18 Third Ave., New York, N.Y. 10028

[21] Appl. No.: 807,253

[22] Filed: Jun. 16, 1977

[51] Int. Cl.² .............................................. A61B 1/00
[52] U.S. Cl. ............................................ 128/12; 32/32
[58] Field of Search ................................. 128/12–20, 128/136; 32/32, 40 R

[56] References Cited

U.S. PATENT DOCUMENTS

| 854,898 | 5/1907 | Lorenz | 128/12 |
|---|---|---|---|
| 892,682 | 7/1908 | Price | 128/12 |
| 1,128,317 | 2/1915 | Jaros | 128/12 |
| 1,474,497 | 11/1923 | Stolper | 128/15 |
| 2,019,060 | 10/1935 | Thibert | 128/12 |

FOREIGN PATENT DOCUMENTS 270,981  2/1950  Sweden ..................... 128/20

OTHER PUBLICATIONS

A New Retractor for Oral Surgical Procedures by U. A. Caorsa, DDS, Dental Digest, Nov. 1945, pp. 620–623.

*Primary Examiner*—Robert W. Michell
*Assistant Examiner*—Henry S. Layton
*Attorney, Agent, or Firm*—Philip H. Gottfried

[57] ABSTRACT

Apparatus is provided for preventing damage to the alveolar ridge and to any teeth, crowns, or dental prosthesis protruding therefrom during the administration of anesthetic and during insertion of rigid instruments into a patient's mouth. A protector is constructed with a removable handle and is arranged to sit astride the maxillary alveolar ridge. The protector is generally "U"-shaped in cross-section, curved to conform to the arc of the maxillary alveolar ridge, and the arms of the "U" are shaped to be located, respectively, within the anterior maxillary labial vestibule and to bear against the hard palate. The depth of the protector prevents the interior thereof from contacting either the maxillary alveolar ridge itself or any protuberances therefrom. When the protector is in place astride the maxillary alveolar ridge, its shape and size diverts the force of any blow received by the protector or any pressure applied to it, away from the maxillary alveolar ridge and toward the maxillary labial vestibule and the hard palate. The handle member which is removably fixed to the protector, is usable in maintaining the protector in position and also usable as an aid in opening a patient's mouth by applying traction thereto during intubation.

14 Claims, 8 Drawing Figures

U.S. Patent    Sept. 12, 1978    4,112,934
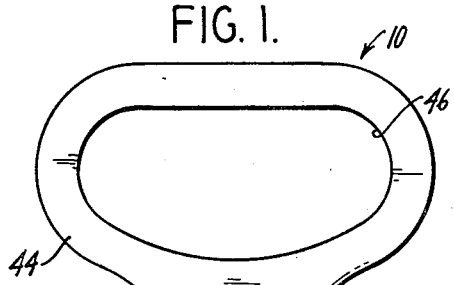
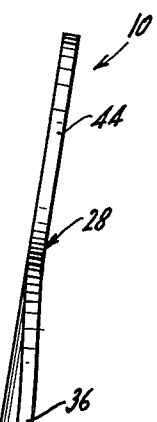
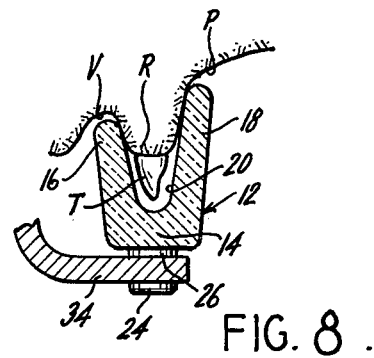
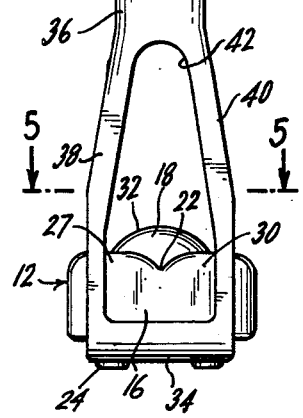
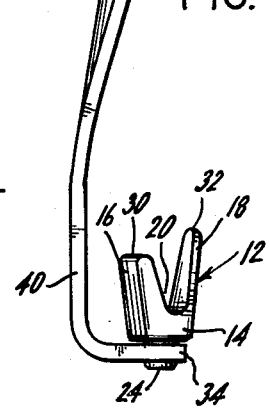
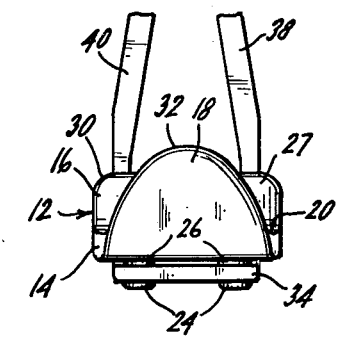
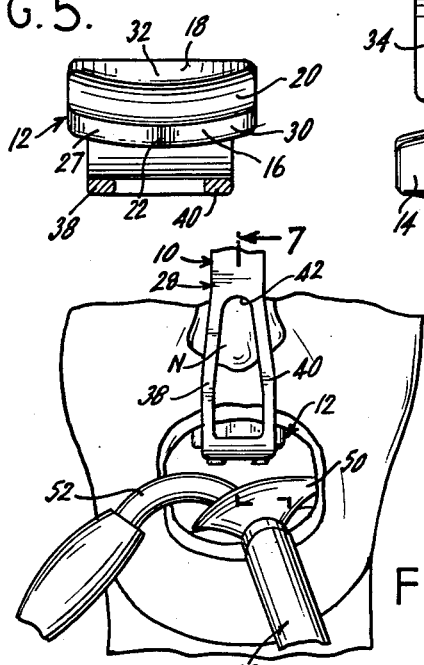
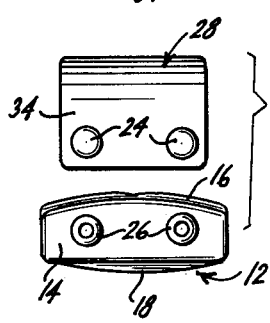
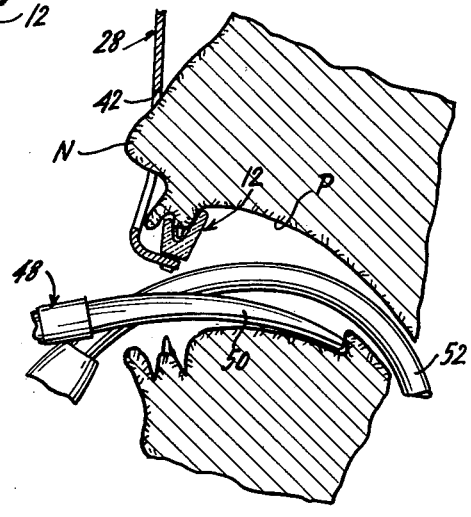

COMBINATION ALVEOLAR RIDGE PROTECTOR AND ANESTHETIC ADMINISTRATION AID

The present invention relates generally to oral protection devices and, in particular, to an apparatus for protecting the maxillary alveolar ridge and any protuberences therefrom from the force of instruments, in the mouth of a patient, bearing thereagainst.

It has long been a problem, when it has been necessary to insert objects into a patient's mouth, to insert those objects properly and without damaging different parts of the mouth. Difficulties encountered inserting objects into the mouth of a patient are compounded when the patient either has an abnormally structured maxilla with a pronounced maxillary alveolar ridge, has abnormally large teeth, dental crowns, or has other dental prostheses.

The appearance of such structures, in addition to rendering the normally difficult task of insertion of necessary instruments and tubes into the mouth of a patient even more difficult, also increases the likelihood that some damage will occur to the teeth, dental prostheses or the maxillary alveolar ridge, either during the insertion of or the retention of instruments within the mouth of a patient.

The damage to a patient's maxillary alveolar ridge or his teeth or dental prostheses during presence in the mouth of various rigid appliances for either transient or sustained periods of time, is a condition which anesthesiologists and surgeons alike have long sought to avoid. Normally, such damage is sought to be avoided by the exercise of extreme care during intubation and rigid endoscopy by anesthesiologists and surgeons. However, in order to properly accomplish intubation, it is necessary for the anesthesiologist to obtain an unobstructed view of the larynx; and, with various surgical procedures, rigid endoscopy is often required using instruments which are quite un-yielding and which, of necessity, must remain in the patient's mouth for extended periods of time.

Often, such rigid instruments, in view of the nature of the operation, must remain in the patient's mouth being supported against the maxillary alveolar ridge itself in the case of lack of teeth thereby causing damage or at least some trauma thereto; and, in the case of teeth and/or dental prostheses protruding therefrom, damaging and even breaking the same.

Despite the existence for some time of the problems discussed hereinbefore, there have not been any satisfactory solutions therefor found. Apparatuses exist which are generally related to the field of either administering anesthetics or which are constructed and arranged for use in the patient's mouth. However, such existing apparatuses do not solve the problems noted hereinbefore.

For example, U.S. Pat. No. 1,128,317 which issued Feb. 16, 1915 illustrates and describes an apparatus for use in administering anesthetics which has, as its main object, the elevation and suspension of the mandible of a patient and the prevention of "tongue swollowing". The apparatus shown and described in the U.S. Pat. No. 1,128,317 in no manner protects the maxillary alveolar ridge or any protuberences therefrom.

In addition, the apparatus of U.S. Pat. No. 1,474,497, which issued Nov. 20, 1923, is of interest. The U.S. Pat. No. 1,474,497 shows an apparatus which is designed to be held by a patient having dental work performed. The apparatus is constructed and arranged to hold and control the tongue, cheek and lips of a patient while the teeth are being treated. Of necessity, the apparatus of the U.S. Pat. No. 1,474,497 must provide access to the teeth of the patient and cannot offer protection to the teeth or the alveolar ridge. The apparatus of the U.S. Pat. No. 1,474,497 is, therefore, not usable to solve the problems noted hereinbefore.

Further, the apparatus of the U.S. Pat. No. 1,474,497 is constructed and arranged, by virtue of its including a tongue piece, to be used on the mandible and would undoubtedly be unusable on the maxilla in view of the interference of the hard palate with the tongue piece.

Still further, the apparatus of the U.S. Pat. No. 1,474,497 is constructed and arranged to rest partially on the lips of the patient and partially on the tongue of the patient and includes a relatively small member which bridges the patient's teeth. In view of the lack of rigidity of the patient's lip and tongue, on which the apparatus would rest, any pressure placed on the apparatus of the U.S. Pat. No. 1,474,497 would cause the bridging member to bear against the patient's teeth thereby permitting just the sort of damage to the teeth or the alveolar ridge which is sought to be prevented.

Accordingly, it is an object of the present invention to provide an apparatus for protecting the alveolar ridge and any protuberences therefrom.

It is a further object of the present invention to provide an apparatus which functions as a protector of the alveolar ridge of a patient and is also usable as an aid in the administration of anesthetic and may be used to facilitate access to the larynx of a patient.

It is a more particular object of the present invention to provide a protector for the alveolar ridge and for the protuberences therefrom which serves to divert any force directed toward the alveolar ridge anteriorly and posteriorly thereof around the ridge and to provide such an apparatus that is simple to manufacture and use and which is economical to produce.

In accordance with an illustrative embodiment demonstrating objects and features of the present invention, there is provided an apparatus for use in preventing damage to the alveolar ridge during insertion of objects into the mouth of the patient and facilitating anesthetic administration. The apparatus comprises a protective member and a handle member. The protective member includes means which are constructed and arranged to straddle the alveolar ridge in a manner to avoid contact therewith and also to avoid contact with any protuberences therefrom. The protective member includes first and second means with the first means being constructed and arranged for receiving force directed toward the alveolar ridge applied to the protective member. The second means is itself constructed and arranged and is constructed and arranged relative to the first means to direct the force received by the first means away from the alveolar ridge. The handle member includes manipulation means which are constructed and arranged to permit the application of force to the protective member through a connecting means. The connecting means is located between the protective member and the handle member and is constructed and arranged relative thereto for permitting force applied to the manipulating means to be transmitted to the protective member.

The above brief description as well as further objects, features and advantages of the present invention will be more fully understood by reference to the following detailed description of the presently preferred but nonetheless illustrative embodiment in accordance with the present invention, when taken in conjunction with the accompanying drawing, wherein:

FIG. 1 is a front elevational view of a representative form of the present invention;

FIG. 2 is a right side elevational view thereof;

FIG. 3 is a fragmentary rear elevational view thereof;

FIG. 4 is an exploded bottom plan view of the fragmentary view of FIG. 3 showing a protective member fashioned in accordance with the present invention separated from a handle member thereof;

FIG. 5 is a sectional view taken substantially along the line 5—5 of FIG. 1 and looking in the direction of the arrows;

FIG. 6 is a fragmentary front elevational view of a representative form of the present invention, on a reduced scale, showing the invention in use in a patient's mouth during intubation;

FIG. 7 is a right sectional elevational view of the representative use of the present invention of FIG. 6 taken substantially along the line 7—7 of FIG. 6 and looking in the direction of the arrows; and, FIG. 8 is a fragmentary sectional elevational side view of part of the subject invention, on an enlarged scale, showing it in position straddling a patient's alveolar ridge and protuberences.

Referring now specifically to the drawing and first to FIG. 1, there is shown an illustrative combination protective apparatus and a handle member embodying objects and features of the present invention, generally designated by the reference numeral 10. A protective member 12 forms part of the apparatus 10, is generally "U"-shaped in cross-section as may be seen by reference to FIG. 8, and is formed with the bottom of the outside of the "U" being generally plane.

The body of the protective member 12 is, as may be most clearly seen in FIGS. 4 and 5, arcuate in the longitudinal direction thereof following a curve which closely approximates the curve of the normal maxillary alveolar ridge. As will be described in greater detail hereinafter, the actual longitudinal dimension of the protective member 12 may vary depending upon the intended use thereof and whether it is to be used in a child or an adult. Further, when the longitudinal extent of the protective member 12 is changed, the degree of curvature thereof may also be changed to conform to different alveolar ridge radii of curvature in those of different age. Still further, as will be discussed in greater detail hereinafter, the depth of the interior of the "U" may change as well on protective members of different size.

The protective member 12 is comprised of three similarly-curved segments all of which follow arcs designed to facilitate use of the protective member as shown in FIGS. 7 and 8. A base segment 14 is generally plane on the lower part thereof as best seen in FIG. 8 and forms the outside of the bottom of the "U"-shape which the protective member 12 presents in cross-section. The left and right "arms" of the "U"-shape as seen in FIG. 8 are composed of arcuate anterior and posterior segments 16, 18 which are joined at their bottoms to the base member 14.

As may be noted by reference to FIGS. 1, 2, 3, 7 and 8, the anterior and posterior arms 16, 18 are of unequal vertical extent for a purpose to be described hereinafter. The anterior arm 16, the base 14 and the posterior arm 18 of the protective member 12 are so connected to one another to define a generally arcuate cavity 20 therebetween which the arms 16, 18 and the base 14 bound on three sides.

While it is to be understood that the apparatus of the present invention is usable to protect the alveolar ridge in the maxilla and in the mandible at various locations, its primary use is in the medial part of the maxillary alveolar ridge in the position shown in FIGS. 6 and 7. In consequence of this usual mode of use of the apparatus 10 of the subject invention, and in consequence of the usual structure of the human mouth, the anterior arm 16 includes a central recess 22 to accomodate and avoid contact with the frenulum when the apparatus is used as shown in FIGS. 6, 7 and 8.

The depth or vertical extent of the cavity 20 is chosen to accomodate the average-sized maxillary alveolar ridge as well as the normal-sized protruding tooth, crown or dental prostheses so that the teeth, crowns or prostheses do not contact the protective member 12 at the bottom of the cavity 20. In addition, the spacing between the anterior and posterior arms 16, 18 is chosen to avoid any contact of the bottom of the cavity with any protrusion from the average maxillary alveolar ridge all for a purpose to be described in detail hereinafter.

The protective member 12 may be supplied in different sizes depending upon the size of the mouth, the size of the maxillary alveolar ridge and the size of the protuberence or protuberences therefrom which are to be protected. With any proposed use of the protective member 12 of the subject invention, the dimensions of the protective member shall be selected to provide clearance between the interior of the cavity 20 and any protuberance from any alveolar ridge which the subject apparatus is to protect.

The anterior arm 16, in the normal or usual position for the protective member 12, abuts the anterior margin of the maxillary alveolar ridge R and is located within the maxillary labial vestibule V which is anterior of the maxillary alveolar ridge R (see FIG. 8). The posterior arm 18 of the protective member 12 is designed to abut the posterior margin of the maxillary alveolar ridge R and abuts the hard palate P as may be seen by reference to FIG. 8.

In view of the normal structure of the maxillary labial vestibule V and the hard palate P, for a reason to be described in detail hereinafter, the anterior and posterior arms 16, 18 of the protective member 12 are sized with the arm 16 shorter than the arm 18 to permit contact of the mucous membrane covering the maxilla in the upper part of the vestibule of the mouth while preventing contact of the interior of the cavity 20 by any protuberence from the maxillary alveolar ridge R.

As noted hereinbefore, the longitudinal extent of the protective member 12 can be varied within reason and the confines of the mouth of a patient on which it is to be used and also depending upon the age and physical size of the patient. However, if the protective member is to be effective when used in the manner described in detail hereinafter, it must be of a longitudinal extent which at least approximates the width of the instrumentation to be introduced into the mouth of the patient.

The protective member 12 is removably fixed by any conventional means, such as by means of male and female snap members 24, 26 to a handle member, generally designated by the reference numeral 28. It is to be understood that the snap members 24, 26 are of conventional design and are merely illustrative of any one of a number of conventional attachment means which could be used to removably fasten the protective member 12 to the handle member 28. The only requirement for the fastening means is that they permit a removable rigid interconnection to be made between the protective member 12 and the handle member 28 and that the connecting means be sterilizable.

Naturally, in view of the proposed use of the subject apparatus, it must be sterilizable in its entirety. Toward that end, the protective member 12 may be fashioned of nylon, one of the several kinds of plastics available or any material which is sterilizable either by the use of heat or chemicals. In addition, the material of which the protective member 12 is fashioned should be somewhat resilient and capable of being formed, by molding or other conventional means, with the uppermost edges thereof, which will contact the mucous membrane covering the maxilla and the upper vestibule of the mouth, being smooth and burr-free to prevent undue abrasion of the mucous membrane when the apparatus is in use in the manner described in detail hereinafter. In a similar manner, the handle member 28 must be fashioned of sterilizable material which should likewise be resilient in view of its manner of use (compare FIG. 2 with FIG. 7).

As may be noted by reference to FIGS. 1 and 3, in view of the recess 22 which is necessary to avoid contact of the anterior arm 16 with the frenulum, two lobes 27, 30 are formed in the anterior arm 16, both of which contact the maxillary labial vestibule V. On the posterior arm 18, a single lobe 32 is formed which rests against the hard palate P. It is the upper surfaces of the lobes 27, 30, 32 which must be rounded to prevent abrasion of the mucous membrane covering the maxilla.

The handle member 28 includes a base 34 which is generally plane and to which the male snap members 24 are fixed for mating with the female snap members 26 on the protective member 12 for fastening the protective member thereto. The snap members 24 are fixed to the base 34 of the handle member 28 by any conventional means such as by being riveted thereto.

At right angles to the base 34, at least in the rest or normal position of the handle 28, is a main body section of the handle 28, generally designated by the reference numeral 36. The main body section 36 bifurcates and forms legs 38, 40, forming a nasal orifice 42 therebetween for a purpose to be described hereinafter. The main body section 36 is joined to a gripping or manipulating section 44 spaced furthest from the base 34 which includes an opening 46 therein designed to accept the hand of a user of the apparatus 10 for use of the subject apparatus in a manner to be described in greater detail hereinafter.

As noted hereinbefore, the material of which the handle member 28 is formed must be sterilizable and, as will be described in detail hereinafter, must be able to withstand tension to which the handle member will be subjected when it is used. In addition, in view of the subject apparatus generally being flexed when in use (compare FIG. 2 with FIG. 7) a certain amount of resiliency of the material of which the handle 28 is formed is desirable. Suggested materials for the handle would be one of the many plastics available, reinforced with a spring steel insert attached thereto; or the handle may be fashioned in its entirety of stainless steel.

In use, a protective member 12 of a longitudinal extent and curvature which is appropriate for the dimensions of the mouth of the patient is selected. The longitudinal extent of the protective member is at least partially selected based upon the type of instruments to be inserted into the mouth of the patient and in particular their transverse dimensions.

The protective member 12, selected according to the criteria noted hereinbefore, is affixed to an appropriately sized handle member 28 such as by mating male and female snap members 24, 26. Both the selected protective member 12 and the selected handle member 28 will have been sterilized before being brought into the operating room where the subject apparatus will be used.

In the use of the apparatus 10 illustrated in FIGS. 6, 7 and 8, the apparatus is shown being used to aid in the administration of anesthetic while serving to protect the maxillary alveolar ridge. The protective member 12 has been inserted in the mouth of the patient with the medial maxillary alveolar ridge within the cavity 20, with the anterior arm 16 within the maxillary labila vestibule V and the posterior arm 18 abutting the hard palate P.

As may be seen by reference to FIGS. 6 and 7, the nose N of the patient protrudes through the nasal orifice 42 in the main body section 36 of the handle member 28 and a moderate amount of traction is applied to the handle member by the user thereof after having placed his hand in the opening 46 in the manipulating section 44. With a patient having a nose N too large to protrude through the nasal orifice 42, the main body section 36 of the handle 28 may be placed astride the nose.

Traction is directed, by pulling up on the handle 28, toward the top of the patient's head, upward as seen in FIGS. 6 and 7.

As may be noted by reference to FIGS. 7 and 8, the tooth T, and usually several teeth of the patient, lie within the cavity 20 of the protective member 12 and do not contact the protective member itself. Similarly, as noted hereinbefore, the size of the protective member 12 is selected to have any other protuberence from the maxillary alveolar ridge not contact the protective member when the apparatus 10 is in place and traction is applied thereto.

A laryngoscope 48 is then inserted in the patient's mouth and the laryngoscope blade 50 is used to depress the tongue of the patient thereby permitting viewing of the larynx and permit insertion of an endotracheal tube 52 for the administration of anesthetic to the patient. If the patient is not to have any work done on him which requires the entry of any further instrumentation into his mouth, the laryngoscope 48 is then withdrawn and the protruding part of the endotracheal tube may be affixed temporarily to the patient, for example, by taping the same to the side of his mouth. The subject apparatus 10 is then also removed from the patient's mouth and damage to the maxillary alveolar ridge and any protuberences therefrom by the laryngoscope 48 has been prevented.

In addition to protecting the maxillary alveolar ridge and any protuberences therefrom from trauma and/or fracture, the traction applied to the handle member 28 in one direction and the traction applied to the laryngoscope in the other direction has also served to facilitate intubation or insertion of the endotracheal tube 52.

In circumstances where rigid endoscopy is to occur after intubation, such as a bronchoscopy or esophagoscopy, after intubation the handle member 28 may be detached leaving the protective member 12 in place in order to continue protection of the maxillary alveolar ridge and protuberences therefrom from contacting the instruments of the surgeon. Typically, in such procedures, the instruments are rested against the maxillary alveolar ridge and/or the protuberences therefrom usually causing trauma thereto. In such instances, the protective member 12 may be held in place by hand after the handle member 28 is detached from the protective member.

Any force which would normally be directed against either the maxillary alveolar ridge or any protuberences therefrom causing the trauma and/or fracture of the protuberences, once the protective member 12 is in place, is diverted by the protective member, in virtue of its construction and arrangement as shown and described hereinbefore, away from the maxillary alveolar ridge and any protuberences and toward the maxillary labial vestibule V and the hard palate P. In view of the lack of any contact between the tooth T or other protuberence from the maxillary alveolar ridge R within the protective member 12, any blows or force received by either the base part 34 of the handle member 28 when it is in place on the base 14, or received by the base itself when the handle member 28 is detached therefrom, never reaches the tooth T or other protuberence or the maxillary alveolar ridge but is directed by the protective member away therefrom thereby preventing damage to the maxillary alveolar ridge.

As will be readily apparent to those skilled in the art, the invention may be used in other specific forms and at other locations within the mouth of a patient without departing from its spirit or essential characteristics. The present embodiment is, therefore, to be considered as illustrative and not restrictive, the scope of the invention being indicated by the claims rather than by the foregoing description, and all changes which come within the meaning and range of equivalence of the claims are therefore intended to be embraced therein.

What is claimed is:

1. An apparatus for use in preventing damage to the alveolar ridge during surgery and for facilitating anesthetic administration, said apparatus comprising a protective member and a handle member, said protective member including means being constructed and arranged to straddle said alveolar ridge in a manner to avoid contact therewith and to avoid contact with protuberances therefrom and including first and second means, said first means being constructed and arranged for receiving force directed toward said alveolar ridge applied to said protective member and said second means being itself constructed and arranged and being constructed and arranged relative to said first means to direct said force received by said first means away from said alveolar ridge, said handle member including manipulation means constructed and arranged for permitting the application of force to said protective member through a connecting means, said connecting means being located between said protective member and said handle member and cooperating therewith and being constructed and arranged relative thereto for permitting force applied to said manipulating means to be transmitted to said protective member.

2. An apparatus according to claim 1, said first and second means including means being constructed and arranged to define a cavity sized to receive said maxillary alveolar ridge and protuberances therefrom without said protuberances contacting said protective member.

3. The apparatus according to claim 2, said cavity being bounded by said first and second means and including an opening, said first means confronting said opening and said second means arranged anteriorly and posteriorly of said opening, said first means being constructed and arranged to confront and avoid contact with any protuberances from said alveolar ridge.

4. The apparatus according to claim 3, said second means including an anterior arm and a posterior arm, said anterior arm being constructed and arranged to be received within the maxillary labial vestibule of a patient and said posterior arm being constructed and arranged relative to said first means and said anterior arm to contact the hard palate of a patient when said anterior arm is located within said maxillary labial vestibule.

5. An apparatus according to claim 1, said protective member being generally "U"-shaped in cross-section with said first means forming the base of said "U"-shape and said second means forming anterior and posterior arms of said "U"-shape and defining a cavity therebetween, said anterior arm of said protective member being constructed and arranged to be received within the maxillary labial vestibule of a patient, said anterior arm said base and said posterior arm being constructed and arranged for said cavity to straddle said maxillary alveolar ridge in a manner to avoid contact with any protuberances therefrom upon said posterior arm contacting the hard palate of a patient.

6. An apparatus according to claim 5, the exterior of said base being generally plane and said anterior arm including a recess therein to accept the frenulum upon said anterior arm being located within said maxillary labial vestibule.

7. The apparatus according to claim 1, said handle member including base means being constructed and arranged to be fixed relative to said protective member, said handle member including a main body part, said second means of said protective member extending in a given direction and said main body part of said handle member extending in said given direction.

8. The apparatus according to claim 7, said handle member including at least a first orifice therein constructed and arranged for permitting at least a part of the nose of a patient to protrude therethrough when said protective member is positioned with said maxillary alveolar ridge and any protuberances therefrom located within said protective member.

9. An apparatus for use in preventing damage to the alveolar ridge during surgery, said apparatus comprising a protective member including means being constructed and arranged to straddle said alveolar ridge in a manner to avoid contact therewith and to avoid contact with protuberances therefrom and including first and second means, said first means being constructed and arranged for receiving force directed toward said alveolar ridge applied to said protective member and said second means being itself constructed and arranged and being constructed and arranged relative to said first means to direct said force received by said first means away from said alveolar ridge.

10. An apparatus according to claim 9, said first and second means including means being constructed and arranged to define a cavity sized to receive said maxillary alveolar ridge and protuberances therefrom without said protuberances contacting said protective member.

11. The apparatus according to claim 10, said cavity being bounded by said first and second means and including an opening, said first means confronting said opening and said second means arranged anteriorly and posteriorly of said opening, said first means being constructed and arranged to confront and avoid contact with any protuberances from said alveolar ridge.

12. The apparatus according to claim 11, said second means including an anterior arm and a posterior arm, said anterior arm being constructed and arranged to be received within the maxillary labial vestibule of a patient and said posterior arm being constructed and arranged relative to said first means and said anterior arm to contact the hard palate of a patient when said anterior arm is located within said maxillary labial vestibule.

13. An apparatus according to claim 9, said protective member being generally "U"-shaped in cross-section with said first means forming the base of said "U"-shape and said second means forming anterior and posterior arms of said "U"-shape and defining a cavity therebetween, said anterior arm of said protective member being constructed and arranged to be received within the maxillary labial vestibule of a patient, said anterior arm said base and said posterior arm being constructed and arranged for said cavity to straddle said maxillary alveolar ridge in a manner to avoid contact with any protuberances therefrom upon said posterior arm contacting the hard palate of a patient.

14. An apparatus according to claim 13, the exterior of said base being generally plane and said anterior arm including a recess therein to accept the frenulum upon said anterior arm being located within said maxillary labial vestibule.

* * * * *